US012590978B2

(12) United States Patent
Ishikura et al.

(10) Patent No.: US 12,590,978 B2
(45) Date of Patent: Mar. 31, 2026

(54) METHOD FOR MEASURING PLATELET ACTIVATION BASED ON SOLUBLE CLEC-2 AND PLATELET COUNT

(71) Applicant: PHC Corporation, Ehime (JP)

(72) Inventors: Hiroyasu Ishikura, Fukuoka (JP); Masahide Kawamura, Tokyo (JP)

(73) Assignee: PHC CORPORATION, Ehime (JP)

( * ) Notice: Subject to any disclaimer, the term of this patent is extended or adjusted under 35 U.S.C. 154(b) by 728 days.

(21) Appl. No.: 17/904,966

(22) PCT Filed: Feb. 26, 2021

(86) PCT No.: PCT/JP2021/007273
§ 371 (c)(1),
(2) Date: Aug. 25, 2022

(87) PCT Pub. No.: WO2021/172493
PCT Pub. Date: Sep. 2, 2021

(65) Prior Publication Data
US 2023/0168260 A1 Jun. 1, 2023

(30) Foreign Application Priority Data
Feb. 28, 2020 (JP) ................................. 2020-032797

(51) Int. Cl.
*G01N 33/53* (2006.01)
*G01N 33/86* (2006.01)

(52) U.S. Cl.
CPC ....... *G01N 33/86* (2013.01); *G01N 2333/705* (2013.01); *G01N 2800/224* (2013.01)

(58) Field of Classification Search
None
See application file for complete search history.

(56) References Cited

U.S. PATENT DOCUMENTS

| | | | |
|---|---|---|---|
| 2009/0029508 A1 | 1/2009 | Yamazaki | |
| 2014/0227265 A1 | 8/2014 | Wu et al. | |
| 2015/0118699 A1 | 4/2015 | Ishikura | |

FOREIGN PATENT DOCUMENTS

| | | | |
|---|---|---|---|
| JP | 2007070359 A | 3/2007 | |
| JP | 4961595 B2 | 4/2012 | |
| JP | 2013228229 A | 11/2013 | |
| JP | 2014070942 A | 4/2014 | |
| JP | 2014520123 A | 8/2014 | |
| JP | 6078845 B2 | 1/2017 | |
| WO | 2010058412 A1 | 5/2010 | |
| WO | 2013168602 A1 | 11/2013 | |

OTHER PUBLICATIONS

Gitz et al., CLEC-2 expression is maintained on activated platelets and on platelet microparticles, Blood, Oct. 2014, vol. 124, No. 14, pp. 2262-2270. (Year: 2014).*

Yamashita et al., Elevated plasma levels of soluble C-type lectin-like receptor 2 (CLEC2) in patients with thrombotic microangiopathy, Thrombosis Research, 178, 2019, pp. 54-58. (Year: 2019).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Van Der Vekiens et al., Human and equine cardiovascular endocrinology: beware to compare, Cardiovascular Endocrinology 2013, vol. 2, No. 4, pp. 67-76. (Year: 2013).*
Fei et al., "Plasma Soluble C-type Lectin-like Receptor-2 is Associated with the Risk of Coronary Artery Disease", Front. Med., vol. 14(1), pp. 81-91. 2020.
Fei et al., "The Production of Soluble C-type Lectin-like Receptor 2 is a Regulated Process", Glycoconj J, vol. 29, pp. 315-321. Jun. 27, 2012.
Inoue et al., "Soluble CLEC-2 is Generated Independently of ADAM10 and is Increased in Plasma in Acute Coronary Syndrome: Comparison with Soluble GPVI", International Journal of Hematology, 11 pages. Jun. 5, 2019.
Ishikura et al., "Blood Kinetics of Novel Platelet Activation Marker Soluble CLEC2 in Patients with Sepsis Patients", Japanese Journal of Thrombosis and Hemostasis, vol. 31, No. 2, p. 224, in Japanese. 2020.
Kazama et al., "Measurement of Soluble C-type Lectin-like Receptor 2 in Human Plasma", Platelets, vol. 26(8), pp. 711-719. 2015.
Yamashita et al., "Elevated Plasma Levels of Soluble C-type Lectin-like Receptor 2 (CLEC2) in Patients with Thrombotic Microangiopathy", Thrombosis Research, vol. 178, pp. 54-58. Mar. 28, 2019.
International Search Report and Written Opinion in International Application No. PCT/JP2021/007273, 10 pages, with partial translation. May 18, 2021.
Feng et al., Common Knowledge Evidence "Modern Clinical Laboratory Diagnostic Manual", Sichuan Science and Technology Press, 1st Edition, 7 pages with translation. Sep. 30, 2013.

(Continued)

*Primary Examiner* — Gary Counts
(74) *Attorney, Agent, or Firm* — Heslin Rothenberg Farley & Mesiti P.C.

(57) ABSTRACT

Provided is a method for assisting in grasping the status of platelet activation, by developing a biomarker that more accurately reflects platelet activation in vivo, said method being usable in testing for thrombotic hemostatic diseases. The method for assisting in grasping the status of platelet activation comprises (1) measuring the concentration of soluble CLEC-2 and a platelet count in a sample obtained from a subject, and (2) calculating a value of [soluble CLEC-2 concentration]/[platelet count] by dividing the soluble CLEC-2 concentration by the platelet count. If desired, the method may further comprise (3) comparing the value with a value of [soluble CLEC-2 concentration]/[platelet count] obtained by using samples from healthy persons.

3 Claims, 3 Drawing Sheets

(56) References Cited

OTHER PUBLICATIONS

Ishikura et al., "Early Recognition of Sepsis-Induced Coagulopathy Using the C2PAC Index: a Ratio of Soluble Type C Lectin-Like Receptor 2 (sCLEC-2) Level and Platelet Count", Platelets, vol. 33(6), pp. 935-944. 2022

Liu et al., Diagnosis and Treatment of Thrombotic Diseases, People's Medical Publishing Housoe, 1st Edition, pp. 50-52, 10 pages with translation. May 31, 2000.

Yagi et al., "Changes of Mean Platelet Volume and Platelet Count in Various Stages of Essential Hypertensives and SHRSP", Med J Kinki Univ, vol. 10, No. 1, pp. 17-24, with abstract. 1985.

* cited by examiner

METHOD FOR MEASURING PLATELET ACTIVATION BASED ON SOLUBLE CLEC-2 AND PLATELET COUNT

CROSS REFERENCE TO RELATED APPLICATIONS

This application is a U.S. National Phase filing under 35 U.S.C. § 371 of International Application PCT/JP2021/007273, filed Feb. 26, 2021, and published as WO 2021/172493 A1 on Sep. 2, 2021. PCT/JP2021/007273 claims priority from Japan application number 2020-032797, filed Feb. 28, 2020. The entire contents of each of these prior applications are hereby incorporated herein by reference.

TECHNICAL FIELD

The present invention relates to a method for measuring platelet activation and a test method for thrombotic hemostatic diseases, based on soluble CLEC-2 and platelet count.

BACKGROUND ART

Thrombi formed in blood vessels are considered to be a significant life-threatening cause factor among a wide range of human diseases. Increased thrombi due to platelet, and accumulation of platelet aggregation cause severe myocardial infarction, chronic unstable angina, transient ischemia, peripheral angiopathy, arterial thrombosis, arteriosclerosis obliterance, pulmonary thromboembolism, or in-stent restenosis. In developed countries, coronary occlusion and cerebral circulation disorder due to thrombi are the leading causes of death, and suppression of thrombosis is an urgent issue worldwide. Furthermore, in the event of a natural disaster, the prevention of deep vein thrombosis and pulmonary embolism (a disease in which venous thrombi flows through blood vessels and occludes the pulmonary artery) during disaster evacuation is being called for, and the preventive efforts are being emphasized. Platelets have granules inside and many membrane glycoproteins on the surface. Platelet activation causes the release of the granules and structural changes in the membrane glycoproteins, and some of them are used as platelet activation markers.

Since platelet factor 4 (PF4) and β-thromboglobulin (βTG) are contained in the α-granule of platelets and are released during with platelet activation, they have been conventionally used as platelet activation markers. However, since the substances in the granules are released even with a slight stimulation such as blood collection, a complicated process, in which blood is collected without a tourniquet using a dedicated blood collection tube containing a platelet activation inhibitor cocktail and a thick blood collection needle of 20 gauge (G) or more and is immediately cooled with ice, is required. In this way, there are many restrictions on blood collection techniques and sample processing, and in addition, it is not widely used clinically from the viewpoint of the reliability of data.

Furthermore, in recent years, membrane glycoproteins cleaved by proteases with platelet activation have become more valuable as platelet activation markers. More particularly, von Willebrand factor (vWF) receptor GPIbα and collagen receptor GPVI are typical molecules, but both have poor knowledge of clinical significance, and it is a kind of ligand-dependent release reaction, and therefore, there are many unclear points as to whether it accurately reflects the activated state of platelets.

CLEC-2 (C-type lectin-like receptor 2) is a platelet-activating receptor belonging to a C-type lectin family identified by Inoue et al. in 2006 (Patent literatures 1 and 2). In addition, recent research results have reported that CLEC-2 is released from the membrane surface with platelet activation and is released as a soluble form (Non-patent literature 1 and Patent literature 3). Furthermore, although a literature on measuring soluble CLEC-2 in several clinical conditions has been published, there are many unclear points about its clinical application (Non-patent literature 2).

CITATION LIST

Patent Literature

[Patent literature 1] JP 4961595 B
[Patent literature 2] JP 2007-070359 A
[Patent literature 3] JP 6078845 B

Non-Patent Literatures

[Non-patent literature 1] Platelets 2015; 26(8): 711-719
[Non-patent literature 2] Thrombosis Research, 2019, Vol. 178, p. 54-58

SUMMARY OF INVENTION

Technical Problem

The object of the present invention is to develop a biomarker that more accurately reflects platelet activation in vivo, and to use it for testing for thrombotic hemostatic diseases.

Solution to Problem

The present inventors have conducted intensive studies to solve the problem. As a result, it was found that the concentration of previously reported soluble CLEC-2 (hereinafter sometimes referred to as sCLEC-2) in plasma reflects the degree of platelet activation in vivo, but accurate diagnosis cannot always be made with CLEC-2 alone. sCLEC-2 is a molecule released from platelets into plasma when platelets are activated, and it was expected that measuring the concentration of sCLEC-2 in plasma would reflect the degree of platelet activation. However, when examined using blood of various clinical conditions, it was found that the plasma sCLEC-2 concentration reflects the platelet activation to some extent, but the concentration also shows a positive correlation with platelet count in blood. The platelet count in blood varies from person to person, and may increase or decrease depending on the clinical conditions. It was found that the plasma sCLEC-2 concentration was low when the platelet count was low even if the platelets were activated, and conversely it was high when the platelet count was high even if the platelet activation was weak, and it might not reflect the degree of platelet activation in vivo. Therefore, the present inventors thought that, if the plasma sCLEC-2 concentration was divided by the platelet count, the amount of sCLEC-2 released per platelet could be measured, and that this index could reflect the platelet activation better, and proceeded with the study. As a result, it was found that [plasma sCLEC-2 concentration]/[platelet count] reflected the clinical conditions of thrombotic diseases better than the plasma sCLEC-2 concentration per se, and found that this index could also be used for testing for thrombotic hemostatic diseases. The above findings have led to the completion of the present invention.

The present invention provides:

[1] A method for assisting in grasping a status of platelet activation, comprising:

(1) measuring a concentration of soluble CLEC-2 and a platelet count in a sample obtained from a subject, and (2) grasping a status of platelet activation from the soluble CLEC-2 concentration and the platelet count.

[2] A method for assisting in grasping a status of platelet activation, comprising:

(1) measuring a concentration of soluble CLEC-2 and a platelet count in a sample obtained from a subject, and (2) calculating a value of [soluble CLEC-2 concentration]/[platelet count] by dividing the soluble CLEC-2 concentration by the platelet count.

[3] The method of [2], further comprising:

comparing the value with a value of [soluble CLEC-2 concentration]/[platelet count] obtained by using a sample from healthy persons.

[4] The method of [2] or [3], wherein the value of [soluble CLEC-2 concentration]/[platelet count] is a marker that reflects clinical conditions of thrombotic hemostatic diseases.

[5] The method of [4], wherein the thrombotic hemostatic disease is any one of disseminated intravascular coagulation (DIC), myocardial infarction, angina pectoris, cerebral infarction, arteriosclerosis obliterance, deep vein thrombosis, pulmonary thromboembolism, cardiogenic cerebral infarction, antiphospholipid antibody syndrome, or sepsis.

[6] The method of any one of [1] to [5], for use as a method for monitoring a prognosis or treatment progress of a thrombotic hemostatic disease in a patient with the thrombotic hemostatic disease.

[7] A system for grasping a status of platelet activation, comprising:

(1) a memory that can store a concentration of soluble CLEC-2 and a platelet count in a sample obtained from a subject, (2) a calculator that can calculate a value of [soluble CLEC-2 concentration]/[platelet count] by dividing the soluble CLEC-2 concentration by the platelet count, (3) a comparison means that can compare the obtained value of [soluble CLEC-2 concentration]/[platelet count] of the subject with a value of [soluble CLEC-2 concentration]/[platelet count] of healthy persons, and (4) a display that can display a result obtained by the comparison.

[8] A system for grasping a status of platelet activation, equipped with a processor and a memory in control of the processor, wherein a program to make a computer perform the following steps is recorded in the memory:

(1) a storage step of storing a concentration of soluble CLEC-2 and a platelet count in a sample obtained from a subject in the memory, (2) a calculation step of calculating a value of [soluble CLEC-2 concentration]/[platelet count] by dividing the soluble CLEC-2 concentration by the platelet count, (3) a comparison step of comparing the value of [soluble CLEC-2 concentration]/[platelet count] obtained in the calculation step with a value of [soluble CLEC-2 concentration]/[platelet count] of healthy persons, and (4) a display step of displaying a result obtained in the comparison step.

[9] Electronic medical records, clinical laboratory equipment, or an in-hospital laboratory system, comprising the system of [7] or [8].

[10] A kit for grasping a status of platelet activation, comprising:

(1) a reagent for measuring soluble CLEC-2 and/or a reagent for measuring platelet, and (2) an instruction manual that describes a relationship between a value of [soluble CLEC-2 concentration]/[platelet count] and a status of platelet activation.

Advantageous Effects of Invention

According to the present invention, the amount of sCLEC-2 released per platelet can be known, and the platelet activation state in blood can be accurately grasped. This makes it possible to fully verify [sCLEC-2 concentration]/[platelet count] and clinical usefulness, and is expected to be used as a marker that reflects the clinical conditions of thrombotic hemostatic diseases. In particular, it is expected to be used as a marker for arterial thrombotic hemostatic diseases, such as myocardial infarction, cerebral infarction, arteriosclerosis obliterance, disseminated intravascular coagulation (DIC), or sepsis, with few effective tests that can be used as arterial thrombotic markers.

DESCRIPTION OF EMBODIMENTS

Figure 1:
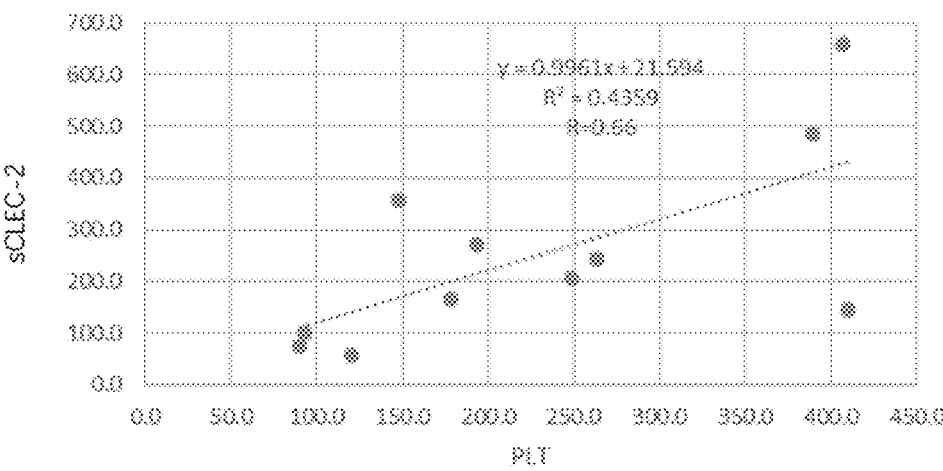
FIG. 1 A graph showing the correlation between a platelet count (PLT) and an sCLEC-2 concentration (sCLEC-2) in non-DIC cases of septic patients (n-DIC), DIC cases of septic patients (DIC), and total septic patients (total sepsis).
Figure 1:
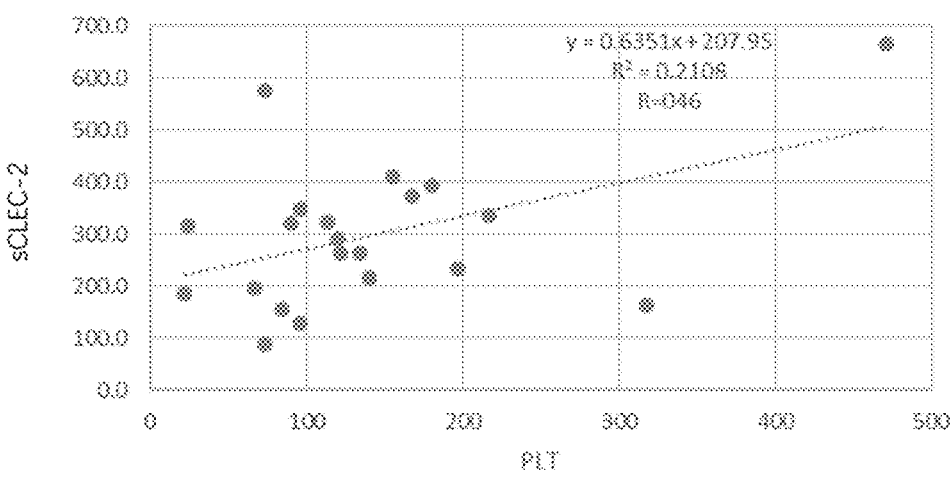
Figure 1:
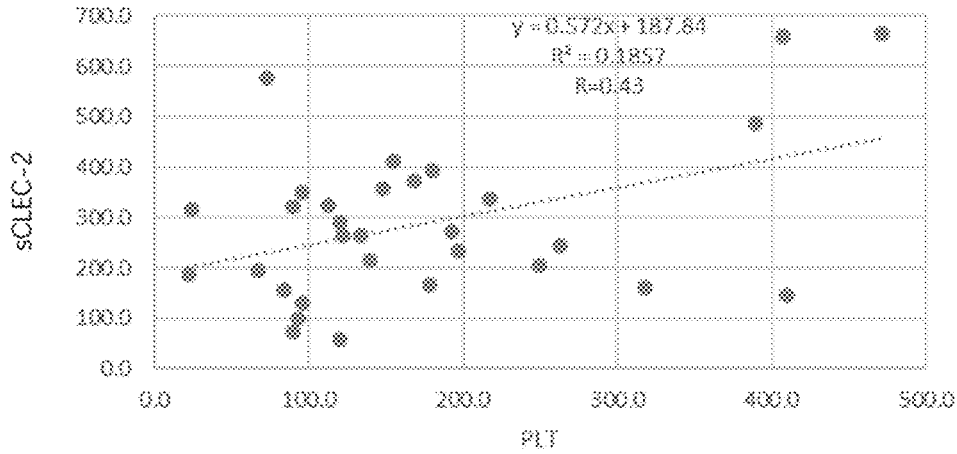

The methods of the present invention include, but are by no means limited to, a method for measuring (or detecting) [soluble CLEC-2 concentration]/[platelet count], a method for assisting in grasping a status of platelet activation, a method for diagnosing (or detecting) thrombotic hemostatic diseases, a method for assisting in a diagnosis of thrombotic hemostatic diseases, a method for measuring (or detecting) [soluble CLEC-2 concentration]/[platelet count] for a diagnosis of thrombotic hemostatic diseases, and the like, and each method includes (1) measuring a concentration of soluble CLEC-2 and a platelet count in a sample obtained from a subject, and (2) grasping a status of platelet activation from the soluble CLEC-2 concentration and the platelet count, more particularly, includes (1) measuring a concentration of soluble CLEC-2 and a platelet count in a sample obtained from a subject, and (2) calculating a value of [soluble CLEC-2 concentration]/[platelet count] by dividing the soluble CLEC-2 concentration by the platelet count, and, if desired, can further include a step of comparing the value with values of [soluble CLEC-2 concentration]/[platelet count] obtained by using samples from healthy persons. The step of grasping a status of platelet activation from the soluble CLEC-2 concentration and the platelet count can be carried out, for example, by calculating a value of [soluble CLEC-2 concentration]/[platelet count], and comparing the value with values of [soluble CLEC-2 concentration]/[platelet count] obtained by using samples from healthy persons, but the status of platelet activation can be comprehensively judged using the soluble CLEC-2 concentration and the platelet count. Hereinafter, an embodiment using the value of [soluble CLEC-2 concentration]/[platelet count] will be mainly explained as an example, but the present invention is not limited to this embodiment.

The term "CLEC-2" as used herein means a platelet activation receptor belonging to a C-type lectin family. CLEC-2 is normally present in the platelet membrane, but is released into the blood with the activation of platelets. The term "soluble CLEC-2 (sCLEC-2)" as used herein means CLEC-2 or a molecule derived from CLEC-2 that is released from such platelets and detected in the blood (in a buffer if it is incubated in the buffer).

sCLEC-2 includes a protein having a molecular weight of approximately 40 kDa, a protein having a molecular weight of approximately 32 kDa, a protein having a molecular weight of approximately 25 kDa, and the like in SDS polyacrylamide gel electrophoresis (SDS-PAGE) under reducing conditions.

It is presumed that the protein having a molecular weight of approximately 40 kDa, and the protein having a molecular weight of approximately 32 kDa are present in the surface of platelet membrane, and are released in the state of being contained in microparticles produced by platelet activation. It is considered that sugar chains are added to these proteins.

On the other hand, it is considered that, with platelet activation, the protein having a molecular weight of approximately 25 kDa is cleaved by protease and released from platelets.

In the present invention, the amount of soluble CLEC-2 as described above is measured. As sCLEC-2, the protein having a molecular weight of approximately 40 kDa, the protein having a molecular weight of approximately 32 kDa, and the protein having a molecular weight of approximately 25 kDa may be detected collectively, or the protein having a molecular weight of approximately 25 kDa may be detected alone.

The sample used for measurement is preferably of human origin, but samples derived from animals other than humans may be used to grasp clinical conditions or the like of experimental animals. The experimental animals are not particularly limited, and examples thereof include a guinea pig, a rat, a mouse, a chinchilla, and the like.

The present invention may be suitably used for testing for thrombotic hemostatic diseases. The term "hemostasis" as used herein means that platelets and coagulation factors are coupled to effectively and properly stop bleeding. The term "thrombotic hemostatic diseases" as used herein include conditions and diseases that include excessive bleeding and abnormal blood coagulation, but are not limited to these. Abnormal blood coagulation is associated with severe coronary insufficiency syndrome, myocardial infarction, unstable angina, refractory angina pectoris, intracoronary thrombotic occlusion after thrombolytic therapy, intracoronary thrombotic occlusion after coronary angioplasty, cerebrovascular diseases due to thrombosis, cerebral infarction, embolic stroke, thrombotic stroke, transient ischemic attack, venous thrombosis, deep vein thrombosis, pulmonary artery embolism, coagulation disorder, disseminated intravascular coagulation, thrombotic microangiopathy, thrombotic thrombocytopenic purpura, obstructive thromboangiitis, thrombosis associated with heparin-induced thrombocytopenia, thrombotic complications due to extracorporeal circulation, thrombotic complications due to cardiac or other intravascular catheters, an intra-aortic balloon pump, or instruments such as arterial stents or heart valves, diseases that require the attachment of artificial organs, antiphospholipid antibody syndrome, and severe infections with thrombotic hemostatic abnormalities such as sepsis, but is not limited to these.

For example, when the value of [sCLEC-2 concentration]/[platelet count] is higher than that of healthy persons or a non-thrombotic hemostatic disease group, it can be said that the patient is likely to have a thrombotic hemostatic disease or is at high risk of developing a thrombotic hemostatic disease. The correlation between the degree of platelet activation represented by the value of [sCLEC-2 concentration]/[platelet count] and various diseases, which is clarified by such comparisons, can be used as standard data.

To give a concrete example, in patients with myocardial infarction or cerebral infarction, the sCLEC-2 concentration and platelet count are measured, and when the ratio becomes high, it can be judged that platelet activation in vivo has occurred, and measures, such as administration or increase in dose of antiplatelet drugs, or additional administration of different types of antiplatelet drugs, can be taken.

In high-risk patients with myocardial infarction or cerebral infarction, such as diabetic patients, it may be possible to measure the sCLEC-2 concentration and platelet count, and administer antiplatelet drugs such as aspirin, as a primary preventive measure, to patients with a high value of [sCLEC-2 concentration]/[platelet count]. In severe infections with thrombotic hemostatic abnormalities, such as sepsis, it can also be used for diagnosis based on the degree of thrombotic hemostatic abnormalities. Furthermore, in patients taking antiplatelet drugs such as aspirin or clopidogrel, it is also possible to measure the sCLEC-2 concentration and platelet count, and when the value is high, to consider increasing the dose of antiplatelet drugs, changing to different types of antiplatelet drugs, or additional administration.

Furthermore, it has been reported that platelet microparticles are an exacerbating factor in rheumatoid arthritis, and since CLEC-2 is also expressed on microparticles, there is a possibility that [sCLEC-2 concentration]/[platelet count] also increases in patients with rheumatoid arthritis, and it may also be useful for testing for rheumatoid arthritis.

Furthermore, it has been reported that CLEC-2 binds to podoplanin, a membrane protein expressed in certain tumor cells, in vivo, and promotes its metastasis. In patients with podoplanin-expressing tumors, there is a possibility that tumors in the blood may activate platelets and [sCLEC-2 concentration]/[platelet count] may increase, and therefore, [sCLEC-2 concentration]/[platelet count] may be used as a cancer metastasis marker.

A method for detecting the presence of sCLEC-2 is not particularly limited, but an immunological method using an antibody that recognizes sCLEC-2 (hereinafter sometimes referred to as "an anti-sCLEC-2 antibody") is preferable. As a method for immunologically detecting a protein, any method known and commonly used per se, for example, an immunoassay using a labeled antibody, such as an enzyme-linked immunosorbent assay (an ELISA method), a chemiluminescence immunoassay, a fluorescent antibody method, a radioimmunoassay, an immunochromatography, or the like; or Western blotting, a latex agglutination method, an immunoturbidimetry method, or the like, can be used, but of these, the immunoassay using a labeled antibody is preferably used from the viewpoint of ease of operation and measurement accuracy. For intraoperative diagnosis, since it is desirable to obtain quick results, the chemiluminescence immunoassay, the immunochromatography, or the like is most preferably used.

The platelet count is usually measured using an automatic blood cell counter (blood counter), but it can also be measured using a blood cell counter and a microscope.

Samples are collected from a subject (in particular, a patient), for example, using a blood collection tube for plasma blood collection. Considering the measurement of platelet count, an EDTA-containing blood collection tube is suitable, but heparin or citric acid-containing one is also possible. Samples for measuring plasma sCLEC-2 concentration and platelet count may be obtained from a single blood collection tube, but if blood is collected at the same time, separate blood collection tubes may be used. The plasma sCLEC-2 concentration is measured, for example, using plasma centrifuged at 2000 g for approximately 20 minutes, but centrifugal conditions are not limited to this, and may be a measurement system using whole blood. Hereinafter, the measurement of plasma sCLEC-2 concentration will be explained as an example, but it is not limited to this. For the platelet count in blood, whole blood containing an anticoagulant, such as EDTA, is used.

The plasma sCLEC-2 concentration is expressed in, for example, pg/mL, and the blood platelet count is expressed in, for example, 1000 cells/mm$^3$, and [sCLEC-2 concentration]/[platelet count] is calculated. The sCLEC-2 concentration used herein can be expressed by an arbitrary unit such as ng/mL or ng/L, and the platelet count can also be expressed by an arbitrary unit such as 10000 cells/mm$^3$, but a unified unit should be used for comparison. By using different units, [sCLEC-2 concentration]/[platelet count] can take different values, but they are essentially the same concept.

The ratio is calculated using a measured value from clinical laboratory equipment that measures the sCLEC-2 concentration and a measured value from a blood counter that measures the platelet count. It is suitable for daily medical care to automatically calculate this calculation on a system connected to both measuring instruments, for example, a hospital laboratory system, a hospital system, or an electronic medical records, but it is also possible to construct a system that connects the data of two measuring instruments, or a machine that can measure the sCLEC-2 concentration and platelet count at the same time. In addition, both data may be used for manual calculation.

The standard data obtained by the present invention is not particularly limited as long as it shows the correlation between [soluble CLEC-2 concentration]/[platelet count] in plasma and the degree of platelet activation or various diseases, but for example, a threshold value for judgment, or original data or statistical processing data for calculating the threshold value for judgment can be mentioned. The standard data may be described in an instruction manual, or may be attached separately as a data sheet. The form of the attached document includes a paper, an electronic medium such as CD-ROM, and download from a homepage or the like.

sCLEC-2 is released into blood with the activation of platelets. The problem with existing platelet activation markers, such as PF4 and βTG, is that the platelet granules are stimulated by the physical pressure of blood sampling and cause non-specific release, but sCLEC-2 is released by a signal transduction-dependent mechanism that induces platelet activation, and it is considered that it will become a marker that more accurately reflects platelet activation in vivo. In addition, sCLEC-2 is a specific marker with few false positives, because CLEC-2 expression is almost limited in the platelet/megakaryocyte system in humans.

Soluble GPVI released by a similar mechanism is potently produced by GPVI receptor-specific agonist stimulation, but other known platelet-activating agonist stimulation has very weak production. That is to say, when the amount of production changes depending on the type of stimulation, it becomes very difficult to interpret it as a marker. However, sCLEC-2 is the most suitable molecule as a quantitative marker of platelet activation, because it is produced at the same level not only by specific agonist stimulation but also by known agonist stimulation.

One of the advantages of this sCLEC-2 is that it is not restricted by blood collection operation. That is to say, unlike PF4 or βTG, which is released by slight stimulation such as blood collection, sCLEC-2 is released by strong platelet activation, and therefore, no special blood collection operation is required. Furthermore, data in which the plasma sCLEC-2 concentration of patients with acute coronary syndrome is significantly higher than that of healthy persons is obtained, and it is highly useful as a monitor for predicting the onset/prognosis and determining the therapeutic effect, and therefore, it is considered to be a dramatically superior marker compared to the conventional activation markers. Additionally, it has also been shown that the sCLEC-2 concentration is elevated in the plasma of patients with cerebral infarction, and that patients with high plasma sCLEC-2 concentration have a poor prognosis.

In the present invention, we have found that the plasma sCLEC-2 concentration has a positive correlation with the blood platelet count. That is to say, the plasma sCLEC-2 concentration tends to be high in individuals with high platelets, and the plasma sCLEC-2 concentration tends to be low in individuals with low platelets. As a result, the plasma sCLEC-2 concentration is affected by the platelet count in blood, and may not necessarily indicate platelet activation.

Therefore, when the plasma sCLEC-2 concentration is divided by the blood platelet count to calculate the amount of sCLEC-2 released per platelet, and thrombotic diseases are diagnosed using this as an index, it is possible to evaluate the degree of platelet activation without depending on the blood platelet count. More particularly, for example, the plasma sCLEC-2 concentration (A) is expressed in pg/mL, and the blood platelet count (B) is expressed in 1000 cells/mm$^3$, and the number obtained by dividing A by B is used as an index of platelet activation.

Disseminated intravascular coagulation (DIC) is a typical thrombotic hemostatic disease in which platelets are activated. In patients with this disease, platelet count decreases with the platelet activation. This clinical condition was investigated using a DIC group with sepsis and a non-DIC group with sepsis based on both the plasma sCLEC-2 concentration and [sCLEC-2 concentration]/[platelet count], and as a result, [sCLEC-2 concentration]/[platelet count] showed higher diagnostic efficiency for DIC. That is to say, [sCLEC-2 concentration]/[platelet count] was significantly higher in the DIC group, whereas the plasma sCLEC-2 concentration was higher in the DIC group than in the non-DIC group, but a statistically significant difference was not obtained. Furthermore, in the DIC group, [sCLEC-2 concentration]/[platelet count] was also significantly correlated with the severity of DIC clinical conditions. Therefore, it can be said that [sCLEC-2 concentration]/[platelet count] is a far more efficient and useful diagnostic index than the plasma sCLEC-2 concentration. In addition, compared with the data of healthy persons, septic patients showed high [sCLEC-2 concentration]/[platelet count] regardless of the presence or absence of DIC. Therefore, it can be said that it is a useful diagnostic index for sepsis, which is a serious infectious disease accompanied by thrombotic hemostatic abnormalities.

This index can determine platelet activity without being affected by the blood platelet count, even in thrombotic hemostatic diseases caused by platelet thrombosis such as acute coronary syndrome (angina pectoris, myocardial infarction) and cerebral infarction, and therefore, it is a more efficient and useful index than the sCLEC-2 concentration.

The present invention includes a system that can be used to carry out the method of the present invention described above; electronic medical records, clinical laboratory equipment, or an in-hospital laboratory system comprising the system; a kit that can be used to carry out the method of the present invention; and the like.

The system of the present invention includes, for example, a system(s) for measuring (or detecting) [soluble CLEC-2 concentration]/[platelet count], a system for grasping a status of platelet activation, a system for assisting in a diagnosis of thrombotic hemostatic diseases, a system for diagnosing (or detecting) thrombotic hemostatic diseases, a system for measuring (or detecting) [soluble CLEC-2 concentration]/[platelet count] for a diagnosis of thrombotic hemostatic diseases, and the like.

Each system of the present invention can comprises (1) a memory that can store concentration of soluble CLEC-2 and a platelet count in a sample obtained from a subject, (2) a calculator that can calculate a value of [soluble CLEC-2 concentration]/[platelet count] by dividing the soluble CLEC-2 concentration by the platelet count, (3) a comparison means that can compare the obtained value of [soluble CLEC-2 concentration]/[platelet count] of the subject with a value of [soluble CLEC-2 concentration]/[platelet count] of healthy persons, and (4) a display that can display a result obtained by the comparison.

Alternatively, each system of the present invention comprises a processor and a memory in control of the processor, wherein a program to make a computer perform the following steps is recorded in the memory: (1) a storage step of storing a concentration of soluble CLEC-2 and a platelet count in a sample obtained from a subject in the memory, (2) a calculation step of calculating a value of [soluble CLEC-2 concentration]/[platelet count] by dividing the soluble CLEC-2 concentration by the platelet count, (3) a comparison step of comparing the value of [soluble CLEC-2 concentration]/[platelet count] obtained in the calculation step with a value of [soluble CLEC-2 concentration]/[platelet count] of healthy persons, and (4) a display step of displaying a result obtained in the comparison step.

The electronic medical records, the clinical laboratory equipment, or the in-hospital laboratory system of the present invention can be equipped with the system of the present invention.

The method of the present invention can be carried out using the system of the present invention, or the electronic medical records, the clinical laboratory equipment, or the in-hospital laboratory system of the present invention (hereinafter referred to the system or the like of the present invention). Regarding "the value of [soluble CLEC-2 concentration]/[platelet count]" that can be measured (or detected) using the system or the like of the present invention; "the condition, diseases, or the like" and "judgement/judgement criteria or the like" thereof that can be grasped using the system or the like of the present invention; and each measurement method or the like of "soluble CLEC-2 concentration and platelet count", the above-mentioned explanations regarding the method of the present invention can be applied as it is.

The kit of the present invention includes, for example, a kit for measuring (or detecting) [soluble CLEC-2 concentration]/[platelet count], a kit for grasping a status of platelet activation, a kit for diagnosing (or detecting) thrombotic hemostatic diseases, and a kit for measuring (or detecting) [soluble CLEC-2 concentration]/[platelet count] for a diagnosis of thrombotic hemostatic diseases.

The kit of the present invention can comprise (1) a reagent for measuring soluble CLEC-2 and/or a reagent for measuring platelet, and (2) an instruction manual that describes a relationship between a value of [soluble CLEC-2 concentration]/[platelet count] and a status of platelet activation.

It is also important to include a [sCLEC-2 concentration]/[platelet count] calculation method in the instruction manual. Using this kit, both the plasma sCLEC-2 concentration and [sCLEC-2 concentration]/[platelet count] can be used as a kit for evaluating platelet activation or a kit for diagnosing hemostatic diseases. If [sCLEC-2 concentration]/[platelet count] is calculated using the reagent kit, diseases such as platelet activation abnormality and thrombosis can be detected easily and quickly when necessary, and the results can be used for discrimination from other diseases or for deciding treatment policies.

The instruction manual included in the kit of the present invention is not particularly limited, as long as it refers to at least the relationship between [plasma sCLEC-2 concentration]/[platelet count] and the degree of platelet activation or various diseases. In addition to the references, the instruction manual can include, for example, a description of procedure for performing immunological measurement using the kit of the present invention, a description of procedure for detecting [plasma sCLEC-2 concentration]/[platelet count] and the degree of platelet activation or various diseases based on the obtained measured values, or precautions regarding storage and handling of the kit itself.

EXAMPLES

The present invention will now be further illustrated by, but is by no means limited to, the following Examples.

Example 1: Measurement of sCLEC-2 Concentration in Human Plasma

The sCLEC-2 concentration (pg/mL) in human plasma in accordance with Example 6 of Japanese Patent No. 6078845.

Mouse anti-human CLEC-2 monoclonal antibodies (1-11D5 and 3-11E6 antibodies) prepared in Examples of Japanese Patent No. 6078845 were used to construct a sandwich ELISA system. More particularly, 1-11D5 antibody (F(ab)′₂) purified with a 0.05 mol/L carbonate buffer (pH 9.5) was diluted to 10 µg/mL, and 100 µL/well of aliquots were added to an immunoassay plate (MAX-ISORP™ NUNC™). After overnight reaction at 4° C., the wells were washed with borate buffered saline (BBS) containing 0.05% polysorbate 20 (Tween® 20) three times, and were blocked with phosphate buffered saline (PBS) containing 1% bovine serum albumin (BSA) by adding 200 µL to each well. Next, standards which were human CLEC-2 (hCLEC-2) protein prepared in Example 3 of Japanese Patent No. 6078845, or measurement samples were diluted with 10% blocking buffer (SUPERBLOCK™), 0.1% sodium octanoate, and 0.14 mol/L sodium chloride/PBS.

When plasma was used as a measurement sample, it was diluted 5 times or more, and 100 μL/well was added and reacted at 37° C. for one and a half hours while shaking, and the wells were washed three times in the same manner. A biotin-labeled 3-11E6 antibody (F(ab)'$_2$-Biotin) prepared in Example 5 of Japanese Patent No. 6078845 was diluted with 10% blocking buffer (SUPERBLOCK™), 0.1% sodium octanoate, and 0.14 mol/L sodium chloride/PBS to 1.0 g/mL, and 100 μL was added to each well. A reaction was carried out at 37° C. for 1 hour while shaking, and the wells were washed three times in the same manner. Next, AMDEX™ streptavidin-conjugated horseradish peroxidase (GE Healthcare) was diluted with 10% blocking buffer (SUPER-BLOCK™), 0.1% sodium octanoate, and 0.14 mol/L sodium chloride/PBS, and 100 μL was added to each well. A reaction was carried out at 37° C. for 1 hour while shaking, and the wells were washed five times in the same manner, and 100 μL of tetramethylbenzidine (TMB) solution was added to each well. A reaction was carried out at room temperature for about 20 minutes, and the reaction was stopped with a 2N sulfuric acid solution. The absorbance at 450 nm (–620 nm) was measured with a plate spectrophotometer (BIO-TEK INSTRUMENTS/EL312e).

Example 2: Measurement of Platelet Count in Human Whole Blood

The platelet count in human whole blood was measured using an automated hematology analyzer (Sysmex, XN-550). The platelet count was expressed in 1000 cells/mm$^3$.

Example 3: Calculation of [sCLEC-2 Concentration]/[Platelet Count]

The measured values of sCLEC-2 count measured in Example 1, the platelet count measured in Example 2, the values of [sCLEC-2 concentration]/[platelet count] calculated from these values are shown in Table 1. The measurement samples were 32 cases of sepsis (20 cases of sepsis with disseminated intravascular coagulation (DIC), and 12 cases of sepsis without DIC, non-DIC), and were diagnosed by the Japanese Association for Acute Medicine "acute DIC diagnostic criteria". In connection with this, each measured value is a measured value of a sample collected on the first day of hospitalization. Furthermore, the sCLEC-2 concentration in plasma and the platelet count in blood were measured in 37 cases of healthy persons, and [sCLEC-2 concentration]/[platelet count] was calculated. Mean±standard deviation of sCLEC-2 concentration, platelet count, and [sCLEC-2 concentration]/[platelet count] in the healthy persons were 87±38.9 (pg/mL), 263±63.4 (1000 cells/mm$^3$), 0.34±0.15, respectively.

TABLE 1

| Non-DIC/DIC | Plasma sCLEC-2 (pg/mL) | Platelet count (1000 cells/mm$^3$) | sCLEC-2/ platelet count |
|---|---|---|---|
| Non-DIC case 1 | 145.9 | 410.0 | 0.4 |
| Non-DIC case 2 | 357.9 | 148 | 2.4 |
| Non-DIC case 3 | 204.8 | 249 | 0.8 |
| Non-DIC case 4 | 99.4 | 93 | 1.1 |
| Non-DIC case 5 | 165.5 | 178 | 0.9 |
| Non-DIC case 6 | 659.2 | 407 | 1.6 |
| Non-DIC case 7 | 485.8 | 389 | 1.2 |
| Non-DIC case 8 | 58.7 | 120.0 | 0.5 |
| Non-DIC case 9 | 271.7 | 193.0 | 1.4 |

TABLE 1-continued

| Non-DIC/DIC | Plasma sCLEC-2 (pg/mL) | Platelet count (1000 cells/mm$^3$) | sCLEC-2/ platelet count |
|---|---|---|---|
| Non-DIC case 10 | 244.4 | 263 | 0.9 |
| Non-DIC case 11 | 74.4 | 90 | 0.8 |
| Non-DIC group Average | 251.6 | 230.9 | 1.10 |
| Non-DIC group Standard deviation | 185.8 | 123.2 | 0.57 |
| DIC case 1 | 336.4 | 217 | 1.6 |
| DIC case 2 | 290.7 | 120 | 2.4 |
| DIC case 3 | 216.2 | 140 | 1.5 |
| DIC case 4 | 372.5 | 168 | 2.2 |
| DIC case 5 | 349.0 | 96 | 3.6 |
| DIC case 6 | 232.4 | 197 | 1.2 |
| DIC case 7 | 129.3 | 96 | 1.3 |
| DIC case 8 | 264.1 | 134 | 2.0 |
| DIC case 9 | 186.1 | 22 | 8.5 |
| DIC case 10 | 665.1 | 471 | 1.4 |
| DIC case 11 | 321.3 | 90 | 3.6 |
| DIC case 12 | 161.9 | 318 | 0.5 |
| DIC case 13 | 156.7 | 84 | 1.9 |
| DIC case 14 | 264.1 | 122 | 2.2 |
| DIC case 15 | 323.4 | 113 | 2.9 |
| DIC case 16 | 194.5 | 67 | 2.9 |
| DIC case 17 | 393.9 | 180 | 2.2 |
| DIC case 18 | 411.2 | 155 | 2.7 |
| DIC case 19 | 576.4 | 73.0 | 7.9 |
| DIC case 20 | 315.1 | 24.2 | 13.0 |
| DIC case 21 | 86.9 | 73 | 1.2 |
| DIC group Average | 297.5 | 141.0 | 3.2 |
| DIC group Standard deviation | 140.2 | 101.4 | 3.0 |
| P value non-DIC vs DIC | 0.25 | 0.035 | 0.0008 |

Figure 2:
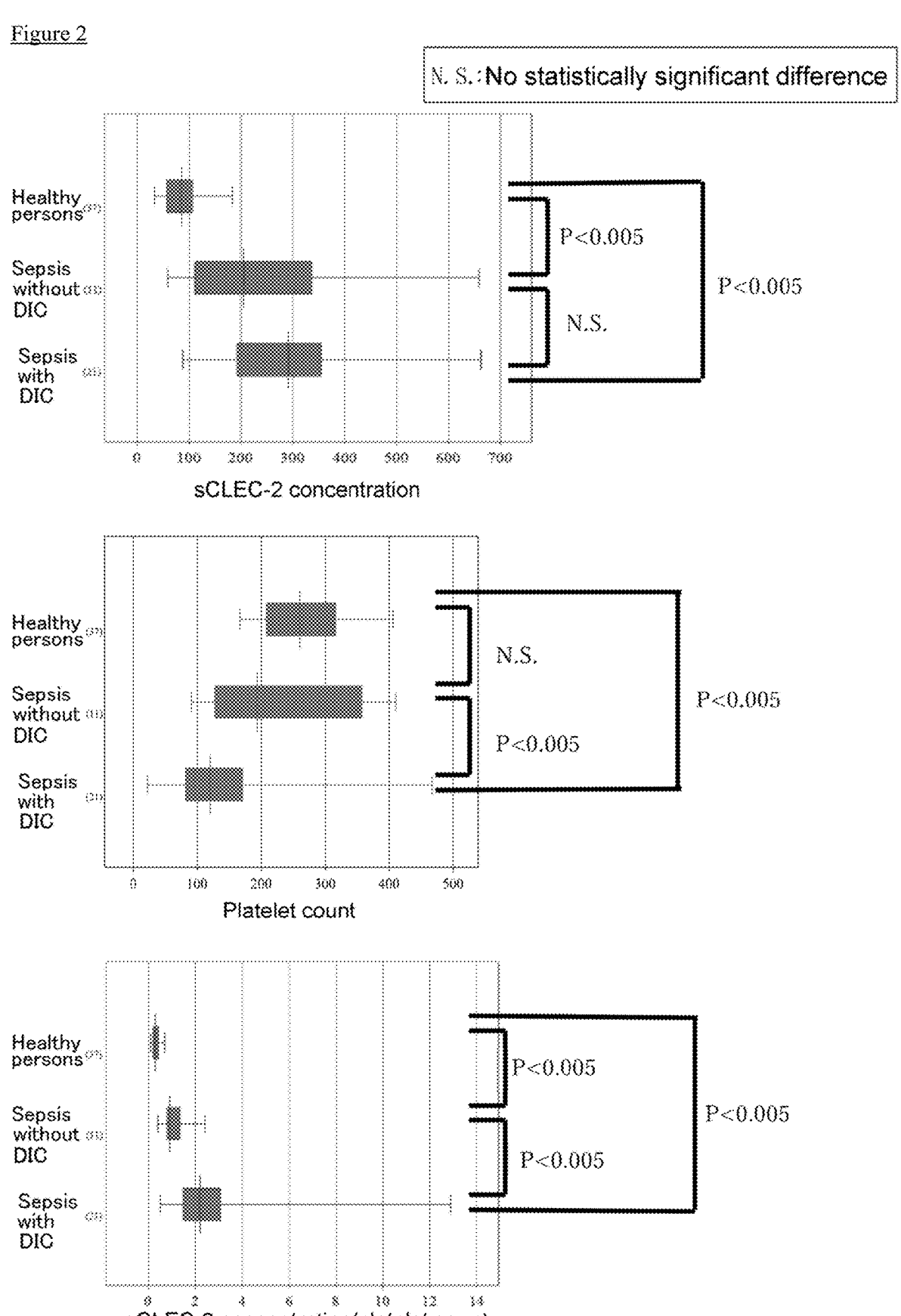
FIG. 2 A graph showing an sCLEC-2 concentration (sCLEC-2), a platelet count (PLT), and [sCLEC-2 concentration]/[platelet count] (sCLEC-2/PLT) in healthy persons, non-DIC cases of septic patients (without DIC), DIC cases of septic patients (with DIC)

For each group of total sepsis patients, DIC cases of sepsis patients (DIC), and non-DIC cases of sepsis patients (n-DIC), when the correlation between the measured value of sCLEC-2 concentration (sCLEC-2) measured in Example 1 and platelet count (PLT) measured in Example 2 was examined, statistically significant correlation was found between the sCLEC-2 concentration and platelet count (FIG. 1). When the value of [sCLEC-2 concentration]/[platelet count] was calculated from the sCLEC-2 concentration and platelet count and compared between the DIC cases of sepsis patients and the non-DIC cases of sepsis patients, it was confirmed that there was no significant difference between the two groups with respect to the sCLEC-2 concentration (p=0.25), but there was a significant difference (p=0.0008) between the two groups with respect to [sCLEC-2 concentration]/[platelet count] (FIG. 2). From this result, sCLEC-2 was affected not only by platelet activation but also by platelet count, and it was confirmed that the amount of sCLEC-2 per platelet count showed platelet activity more accurately. Furthermore, in the case of sepsis, the sCLEC-2 concentration and [sCLEC-2 concentration]/[platelet count] were higher than those of healthy persons regardless of the presence or absence of DIC, and it was shown that these were also useful for the diagnosis of sepsis.

Example 4: Evaluation as Biomarker Based on ROC Curve

Figure 3:
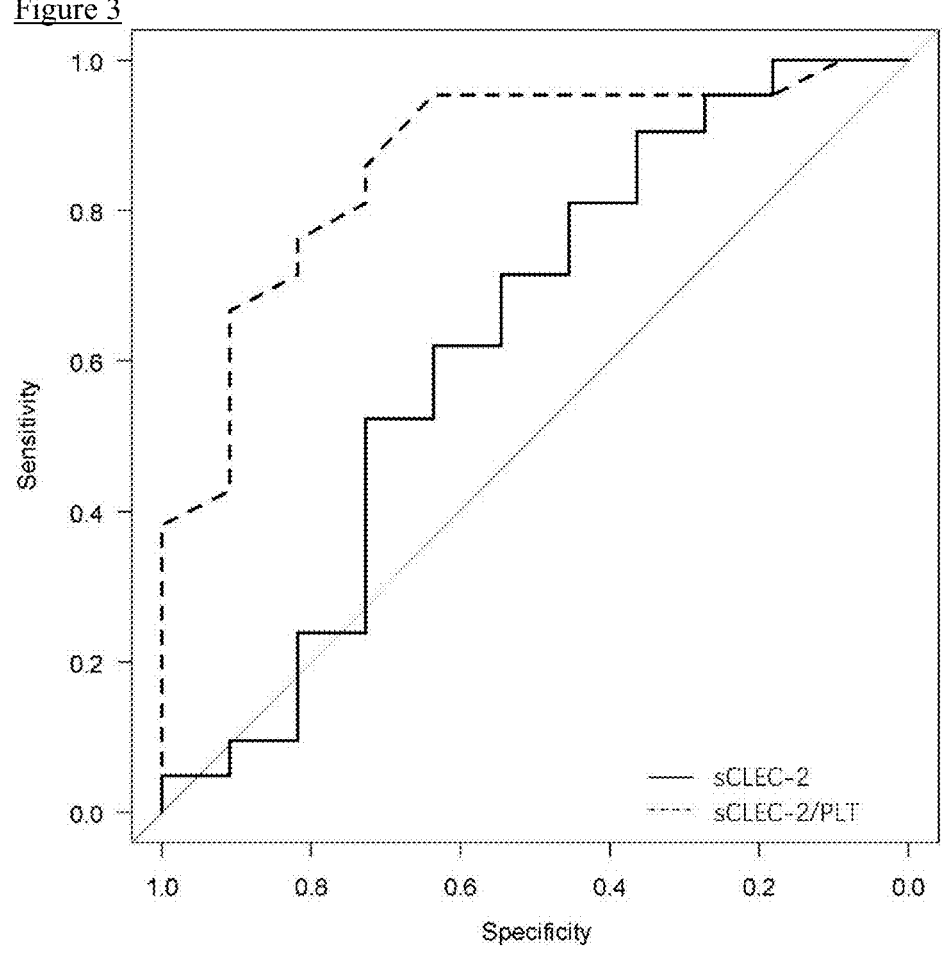
FIG. 3 ROC curves for a sCLEC-2 concentration (solid line) and [sCLEC-2 concentration]/[platelet count](dotted line).

The measured values and the calculated values obtained in Example 3 were used to create an ROC (Receiver Operatorating Characteristic) curve and calculate the area under the curve (AUC). FIG. 3 shows the result of the sCLEC-2 concentration (solid line) and the result of [sCLEC-2 concentration]/[platelet count](dotted line). The AUC of the ROC curve was 0.628 for sCLEC-2 concentration, 0.866 for [sCLEC-2 concentration]/[platelet count], and 0.732 for platelet count. It is said that the closer the AUC is to 1.0, the higher the diagnostic ability, and [sCLEC-2 concentration]/[platelet count] showed the best diagnostic ability.

INDUSTRIAL APPLICABILITY

The present invention can be used to grasp the status of platelet activation, and can be used for testing for thrombotic hemostatic diseases or the like.

The invention claimed is:

1. A method for grasping a status of platelet activation, comprising:

obtaining or having obtained one or more samples from a human subject, wherein the one or more samples are plasma and/or whole blood;

measuring a concentration of soluble CLEC-2 and a platelet count in the one or more samples, wherein the platelet count is measured from a whole blood sample and the concentration of soluble CLEC-2 is measured from a plasma sample or the whole blood sample;

calculating a ratio of the concentration of soluble CLEC-2 to the platelet count in the one or more samples to identify the human subject as having or at risk of having a thrombotic hemostatic disease; and administering a treatment to the human subject, wherein the treatment is an antiplatelet agent capable of treating the thrombotic hemostatic disease.

2. The method according to claim 1, further comprising, method for monitoring a prognosis or treatment progress of a thrombotic hemostatic disease in the human subject, wherein monitoring comprises:

obtaining or having obtained one or more additional samples from the human subject;

measuring a concentration of soluble CLEC-2 and a platelet count in the one or more additional samples;

calculating a ratio of the concentration of soluble CLEC-2 to the platelet count in the one or more additional samples; and comparing the ratio of the concentration of soluble CLEC-2 to the platelet count in the one or more additional samples to the ratio of the concentration of soluble CLEC-2 to the platelet count in the one or more samples.

3. The method according to claim 1, wherein the thrombotic hemostatic disease is any one of disseminated intravascular coagulation (DIC), myocardial infarction, angina pectoris, cerebral infarction, arteriosclerosis obliterance, deep vein thrombosis, pulmonary thromboembolism, cardiogenic cerebral infarction, antiphospholipid antibody syndrome, or sepsis.

* * * * *